US012083126B2

(12) United States Patent
Saadeh

(10) Patent No.: US 12,083,126 B2
(45) Date of Patent: *Sep. 10, 2024

(54) PHARMACEUTICAL COMPOSITIONS AND METHODS FOR ANESTHESIOLOGICAL APPLICATIONS

(71) Applicant: Melt Pharmaceuticals, Inc., Nashville, TN (US)

(72) Inventor: Dennis Elias Saadeh, Brentwood, TN (US)

(73) Assignee: MELT PHARMACEUTICALS, INC., Brentwood, TN (US)

( * ) Notice: Subject to any disclaimer, the term of this patent is extended or adjusted under 35 U.S.C. 154(b) by 209 days.

This patent is subject to a terminal disclaimer.

(21) Appl. No.: 17/732,667

(22) Filed: Apr. 29, 2022

(65) Prior Publication Data

US 2022/0249510 A1 Aug. 11, 2022

Related U.S. Application Data

(63) Continuation of application No. 16/899,353, filed on Jun. 11, 2020, now abandoned, which is a continuation-in-part of application No. 16/250,450, filed on Jan. 17, 2019, now abandoned, which is a continuation-in-part of application No. 15/995,875, filed on Jun. 1, 2018, now Pat. No. 10,391,102, which is a continuation-in-part of application No. 15/903,529, filed on Feb. 23, 2018, now Pat. No. 10,166,240, and a continuation-in-part of application No. 15/903,615, filed on Feb. 23, 2018, now Pat. No. 10,179,136, said application No. 15/903,529 is a continuation-in-part of application No. 15/184,768, filed on Jun. 16, 2016, now Pat. No. 9,918,993, said application No. 15/903,615 is a continuation-in-part of application No. 15/184,768, filed on Jun. 16, 2016, now Pat. No. 9,918,993.

(60) Provisional application No. 62/182,130, filed on Jun. 19, 2015.

(51) Int. Cl.
*A61K 31/551* (2006.01)
*A61K 31/135* (2006.01)
*A61K 31/138* (2006.01)
*A61K 31/4178* (2006.01)
*A61K 47/38* (2006.01)

(52) U.S. Cl.
CPC .......... *A61K 31/551* (2013.01); *A61K 31/135* (2013.01); *A61K 31/138* (2013.01); *A61K 31/4178* (2013.01); *A61K 47/38* (2013.01)

(58) Field of Classification Search
CPC .............. A61K 2300/00; A61K 31/135; A61K 31/138; A61K 31/5517; A61K 31/4178; A61K 45/06; A61K 9/0031; A61K 31/403; A61K 47/10; A61K 47/22; A61K 47/26; A61K 47/34; A61K 47/42; A61K 47/44; A61K 9/0014; A61K 9/0019; A61K 9/0043; A61K 9/0053; A61P 23/02
See application file for complete search history.

(56) References Cited

U.S. PATENT DOCUMENTS

| | | | |
|---|---|---|---|
| 4,246,894 A | 1/1981 | Hamacher | |
| 4,671,953 A | 6/1987 | Stanley et al. | |
| 6,069,143 A | 5/2000 | Ali et al. | |
| 7,309,721 B2 | 12/2007 | Budhu et al. | |
| 7,700,588 B2 * | 4/2010 | Merkus ............... | A61K 9/0043 540/562 |
| 7,893,040 B2 | 2/2011 | Loftsson | |
| 8,217,033 B2 | 7/2012 | Gizurarson | |
| 8,809,322 B2 | 8/2014 | Gizurarson | |
| 9,918,993 B2 | 3/2018 | Berdahl et al. | |
| 9,956,211 B2 | 5/2018 | Andersen et al. | |
| 10,166,240 B2 | 1/2019 | Berdahl et al. | |
| 10,391,102 B2 | 8/2019 | Berdahl et al. | |
| 2003/0185872 A1 | 10/2003 | Kichinke | |
| 2007/0116764 A1 | 5/2007 | Marunaka et al. | |
| 2009/0061024 A1 | 3/2009 | Eppler et al. | |
| 2009/0175939 A1 | 7/2009 | Bosse et al. | |
| 2009/0306051 A1 | 12/2009 | Meyerson et al. | |
| 2011/0054038 A1 | 3/2011 | Glozman | |
| 2013/0158016 A1 | 6/2013 | Enrique | |
| 2013/0345202 A1 | 12/2013 | Amselem | |
| 2014/0079740 A1 | 3/2014 | Salama | |

(Continued)

FOREIGN PATENT DOCUMENTS

| | | |
|---|---|---|
| JP | H10-500664 A | 1/1998 |
| JP | H11-500729 A | 1/1999 |

(Continued)

OTHER PUBLICATIONS

Office Action issued in U.S. Appl. No. 17/116,277 mailed Jun. 23, 2023, 11 pages.
Office Action in EP Application No. 16812447.7 mailed Jul. 13, 2023, 4 pages.
PCT/US2016/037893 International Search Report and Written Opinion dated Sep. 7, 2016.
Chia et al. "Role of .beta.-blockade in anaesthesia and postoperative pain management after hysterectomy," British Journal of Anaesthesia, 2004, 93(6):799-805.
Davis et al. "Effect of Antiemetic Therapy on Recovery and Hospital Discharge Time." Anesthesiology, 1995, 83:956-960.
Ramaiah et al. "Pediatric procedural sedation and analgesia outside the operating room: anticipating, avoiding and managing complications," Expert Rev. Neurother, 2011, 11(5):755-763.

(Continued)

*Primary Examiner* — Savitha M Rao
(74) *Attorney, Agent, or Firm* — POLSINELLI PC

(57) ABSTRACT

Pharmaceutical compositions and methods for inducing conscious sedation using such compositions are described, the compositions including a benzodiazepine-based compound, an NMDA antagonist, and optionally a β-blocker, antiemetic, an NSAID, and/or an antihistamine medication. Compositions may be incorporated into vehicles for extended release. Methods for fabricating the compositions and using them for anesthesiological applications are also described.

16 Claims, No Drawings

(56) References Cited

U.S. PATENT DOCUMENTS

| | | |
|---|---|---|
| 2015/0374653 A1 | 12/2015 | Hou |
| 2016/0367566 A1 | 12/2016 | Berdhal et al. |
| 2018/0177796 A1 | 6/2018 | Berdahl et al. |
| 2018/0177797 A1 | 6/2018 | Berdahl et al. |
| 2018/0271877 A1 | 9/2018 | Berdahl et al. |
| 2018/0303847 A1 | 10/2018 | Baum et al. |
| 2019/0142841 A1 | 5/2019 | Saadeh |
| 2020/0155568 A1 | 5/2020 | Berdahl et al. |

FOREIGN PATENT DOCUMENTS

| | | |
|---|---|---|
| WO | 95/22965 A2 | 8/1995 |
| WO | 96/25925 A1 | 8/1996 |
| WO | 2005/023226 A1 | 3/2005 |
| WO | 2011/161439 A1 | 12/2011 |
| WO | 2014/020155 A1 | 2/2014 |
| WO | 2018/025089 A2 | 2/2018 |

OTHER PUBLICATIONS

Tobias et al. "Procedural sedation: A review of sedative agents, monitoring, and management of complications," Saudi J Anaesth., 2011, 5(4):395-410.
McLean et al. "The pharmacological treatment of nystagmus: a review," Expert Opinion on Pharmacotherapy, 2009, 10(11):1805-1816.
MacDonald et al. "Central Positional Nystagmus: A Systematic Literature Review," Frontiers in Neurology, Apr. 2017, 8:1-11.
JP2017-566010 Office Action dated Jun. 5, 2018.
KR10-2018-7000815 Office Action dated Aug. 2, 2018.
Louon et al. "Sedation with Nasal Ketamine and Midazolam for Cryotherapy in Retinotherapy of Prematurity", British Journal of Ophthalmology, 1993, 77:529-530.
Roelofse et al. "Pediatric procedural sedation and analgesia outside the operating room: anticipating, avoiding and managing complications," Expert Rev. Neurother, 2011, 11(5):755-763.
Rudnic et al., "Oral Solid Dosage Forms." Remington: The Science and Practice of Pharmacy, 19th edition, vol. II, 1995, Chapter 92, 1615-1649.
Holm et al. "In vitro, ex vivo and in vivo examination of buccal absorption of metoprolol with varying pH in TR146 cell culture, porcine buccal mucosa and Gottingen minipigs," European Journal of Pharmaceutical Sciences, 2013, 49:117-124.
Wang et al. "Improving sublingual delivery of weak base compounds using pHmax concept: Application to propranolol," European Journal of Pharmaceutical Sciences, 2010, 39:272-278.
Golpayegani et al. "Comparison of oral Midazolam-Ketamine and Midazolam-Promethazine as sedative agents in pediatric dentistry," Dental Research Journal, Jan. 2012, 9(1):36-40.
Rosenberg et al. "General Anesthesia," Anesth Prog, 1991, 38:172-186.
EP16812447.7 Extended European Search Report dated Jan. 17, 2019.
Beebe et al. "Effectiveness of Preoperative Sedation with Rectal Midazolam, Ketamine, or Their Combination in Young Children," Anesthesia & Analgesia, Dec. 1992, 75(6):880-884.
Katz et al. "Haemodynamic Stability and Ketamine-Alfentanil Anaesthetic Induction," British Journal of Anaesthesia, 1998, 81:702-706.
Khatavkar et al. "Comparison of Nasal Midazolam with Ketamine versus Nasal Midazolam as a Premedication in Children," Saudi Journal of Anesthesia, 2014, 8(1):17-21.
Lokken et al. "Conscious Sedation by Rectal Administration of Midazolam or Midazolam Plus Ketamine as Alternatives to General Anesthesia for Dental Treatment of Uncooperative Children," European Journal of Oral Sciences, Oct. 1994, 102(5):274-280.
Novak et al. "Sedation with Ketamine and Low-Dose Midazolam for Short-Term Procedures Requiring Pharyngeal Manipulation in Young Children," Paediatric Anaesthesia, Jan. 2008, 18(1):48-54.
Smith et al. "Prevention of Vomiting after General Anesthesia for Pediatric Ophthalmic Surgery," American Association of Nurse Anesthesists Journal, Feb. 2001, 69(1):39-43.
Warner et al. "Ketamine Plus Midazolam, a Most Effective Paediatric Oral Premedicant," Paediatric Anaesthesia, 1995, 5(5):293-295.
PCT/US2019/034034 International Search Report and Written Opinion mailed Sep. 17, 2019.
JP2019-010699 Notice of Reasons for Rejection mailed Jan. 7, 2020.
PCT/US/2020/013116 International Search Report and Written Opinion mailed Mar. 24, 2020.
Office Action in U.S. Appl. No. 17/116,277 mailed Feb. 15, 2023, 12 pages.
Examination Report in related EP Application No. 16812447.7 dated May 9, 2022, 5 pages.

* cited by examiner

PHARMACEUTICAL COMPOSITIONS AND METHODS FOR ANESTHESIOLOGICAL APPLICATIONS

CROSS REFERENCE TO RELATED APPLICATION(S)

This is a continuation patent application claiming the benefit of priority under 35 U.S.C. § 120 to U.S. patent application Ser. No. 16/899,353, filed Jun. 11, 2020, now pending, which is a continuation-in-part of U.S. patent application Ser. No. 16/250,450, filed Jan. 17, 2019, now abandoned, which is a continuation-in-part of U.S. patent application Ser. No. 15/995,875, filed Jun. 1, 2018, now issued as U.S. Pat. No. 10,391,102, which is a continuation-in-part of U.S. patent application Ser. No. 15/903,529, filed Feb. 23, 2018, now issued as U.S. Pat. No. 10,166,240, which is a continuation-in-part of U.S. patent application Ser. No. 15/184,768, filed Jun. 16, 2016, now issued as U.S. Pat. No. 9,918,993, which in turn claims the benefit of priority under 35 U.S.C. § 119(e) of U.S. provisional patent application No. 62/182,130, filed Jun. 19, 2015, the entire content of each of which is incorporated herein by reference. U.S. patent application Ser. No. 15/995,875, filed Jun. 1, 2018, is also a continuation-in-part claiming the benefit of priority under 35 U.S.C. § 120 to U.S. patent application Ser. No. 15/903,615, filed Feb. 23, 2018, now issued as U.S. Pat. No. 10,179,136, which is a continuation-in-part of Ser. No. 15/184,768, filed Jun. 16, 2016, now issued as U.S. Pat. No. 9,918,993, which claims the benefit of priority under 35 U.S.C. § 119(e) of U.S. provisional patent application No. 62/182,130, filed Jun. 19, 2015, the entire content of each of which is incorporated herein by reference.

FIELD OF THE INVENTION

The present invention relates generally to the field of pharmacology and more specifically to compositions having anesthetic properties that are useful in various kinds of medical practice, such as surgery, and to methods of preparing and using such compositions.

BACKGROUND

The present disclosure relates to solid or liquid pharmaceutical formulations comprising combinations of active agents such as anesthetics, anti-emetics, blood pressure, anti-anxiety medications and/or analgesics, and methods for using the same for providing anesthesia by administering such compositions orally, including such administrations as sublingual or buccal. The formulations may also include slow release reversal agents that would counteract the initial anesthesia effect.

It is necessary in many cases to use local anesthesia, particularly via oral route in the course of various surgical procedures, e.g., ophthalmic surgeries or urological interventions. For instance, when local anesthesia is employed during or prior to intraocular operations, the occurrences of pain, anxiety, peri-operative stress, nausea, agitation, vomiting and the like are less frequent, which will typically have a very beneficial effect on the surgical experience and reducing the number of intraocular complications such as bleeding, secretions, cardiac and/or pulmonary complications, etc. The severity of those complications when they do occur will also be less pronounced when local anesthesia is used.

Traditionally, an intravenous route is used to administer medications. Alternatives to intravenous methods and therapies have been suggested and previously used for the treatment. In particular, oral administration of benzodiazepines, opioid analgesics, propofol, ketamine or etomidate utilizing the MAC procedure (monitored anesthesia care) has been suggested and tried, but no more than minimal to moderate improvement has been achieved by such methods. Therefore, there remains a need for better treatments of these disorders.

This patent specification discloses such pharmaceutical compositions suitable for anesthesiological applications that can achieve positive patient outcomes while free of drawbacks and deficiencies of existing methods and formulations. Methods of fabricating and administering the same are also discussed.

SUMMARY

According to one embodiment of the invention, there are provided pharmaceutical compositions. The compositions include a therapeutically effective quantity of at least one pharmaceutically active compound of the first class comprising benzodiazepine moiety or pharmaceutically acceptable salts, hydrates, solvates or N-oxides thereof, a therapeutically effective quantity of at least one pharmaceutically active compound of the second class that is an NMDA antagonist or pharmaceutically acceptable salts, hydrates, solvates or N-oxides thereof, and at least one pharmaceutically acceptable excipient or carrier therefor.

According to another embodiment of the invention, the pharmaceutical compositions described above may further include a therapeutically effective quantity of at least one pharmaceutically active compound of the third class that is a β-blocker, a nonsteroidal anti-inflammatory drug (NSAID), or an antiemetic medicament, or a combination thereof, or pharmaceutically acceptable salts, hydrates, solvates or N-oxides thereof.

According to further embodiments of the invention, in the pharmaceutical compositions described above, the pharmaceutically active compound of the first class may be any of midazolam, diazepam, lorazepam, flunitrazepam, alprazolam, chlordiazepoxide, clonazepam or clorazepate, the pharmaceutically active compound of the second class may be any of ketamine, dextrorphan, etomidate, methadone, memantine, amantadine or dextromethorphan and the pharmaceutically active compound of the third class may be (if a (3-blocker) any of metoprolol, propranolol, acebutolol, nadolol, atenolol, betaxolol, esmolol, bisoprolol fumarate, carvedilol, nebivolol, penbutolol, timolol, or sotalol or (if an antiemetic) ondansetron, dolasetron, granisetron, palonosetron, promethazine, imenhydrinate, or meclizine.

According to yet another embodiment of the invention, there are provided further pharmaceutical compositions such as any described above, wherein the compositions are formulated as a liquid or a solid item, e.g., a troche, a lozenge, a capsule, a pill, a cap and a bolus suitable for sublingual or oral administration.

According to other embodiments, there are provided specific compounds for making the compositions described above, for example, midazolam, ketamine and ondansetron, as well as methods for using above-mentioned composition(s) for the purposes of local anesthesia in various applications, such as ophthalmic surgery.

According to further embodiments of the invention, the above-mentioned methods of using the composition(s) include orally administering to a patient in need thereof (i.e., those patients who require conscious sedation or pre-sedation) a pharmaceutical composition described herein as the first step of a medical or surgical procedure, the procedure being an ophthalmic surgery (e.g., a cataract, glaucoma, corneal, eyelid surgery, or retinal surgery), a dental procedure (e.g., a tooth extraction, an oral surgery, or a root canal surgery), an outpatient medical procedure (e.g., medical imaging procedure, biopsy, bone marrow harvesting, colonoscopy, or endoscopy), a urological procedure, a laparoscopic procedure, obstetric and gynecological procedures, a gastrointestinal procedure, an otolaryngological procedure, a cosmetic surgery procedure, a dermatological procedure, a podiatric procedure, an orthopedic procedure, an emergency medical treatment, a psychiatric treatment, or a veterinarian procedure.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of disease or pathology.

The terms "anesthetic," "anesthesia," "anesthesiology" and the like refer herein to substances, compounds, processes or procedures that induce insensitivity to pain such as a temporary loss of sensation.

The term "conscious sedation," which for the purposes of this application, may be used interchangeably with terms "procedural sedation" and "analgesia" is used herein to refer to an induced state of sedation characterized by a minimally depressed consciousness such that the patient is able to continuously and independently maintain a patent airway, retain protective reflexes, and remain responsive to verbal cues and/or tactile or physical stimulation.

Conscious sedation is typically performed/induced to decrease the level of anxiety in a patient and to elicit an improved degree of cooperation from the patient prior to or during a procedure. Conscious sedation, therefore, refers to a condition that is medically different and distinct from deep sedation which is the next level of sedation defined as depression of consciousness when the patient's ability to independently maintain ventilatory function may be impaired and he or she cannot be easily aroused; however, the patient will still purposefully respond to repeated or painful stimulation.

Conscious sedation is also clearly distinguishable for the purposes of the present application from the lower level of sedation (i.e., minimal sedation when the patient is able to maintain a normal response to verbal stimuli) as well as the highest level of sedation (i.e., general anesthesia when there is no response from the patient even with painful stimulus).

The term "pre-sedation" is defined for the purposes of this application as conscious sedation that is induced some time before a procedure, e.g., between about 5 minutes and about 1 hour prior.

The terms "solvate" and "hydrate" are used herein to indicate that a compound or substance is physically or chemically associated with a solvent for "solvates" such as water (for "hydrates").

The term "NMDA antagonist" is defined as a compound that inhibits ("antagonizes") the action of the N-methyl-D-aspartate receptors and is inclusive of both competitive and non-competitive antagonists, glycine antagonists and uncompetitive channel blockers, as these terms are understood by those having ordinary skill in the art.

The term 13-blocker" refers to a compound of any kind that can prevent or reduce the stimulation of the adrenergic receptors responsible for increased cardiac action.

The term "antiemetic" is defined as a drug or medicament that treats, reduces, and/or prevents nausea and/or vomiting.

The term "non-steroid anti-inflammatory drug" or "NSAID" refers to a class of compounds that are free of any steroid moieties yet are capable of providing analgesic, antipyretic and/or anti-inflammatory effects.

The term "antihistamine medicament" refers to any compound that is capable of inhibiting or counteracting the physiological effects of histamine.

The term "polyglycol" is defined as a polymer or oligomer containing several ether-glycol linkages that yields one or more glycols when these linkages are cleaved, e.g., by hydrolysis.

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "binder" refers to a substance or compound that promotes, provides or improves cohesion, i.e., a substance that causes the components of a mixture to cohere to form a solid item that possesses integrity.

The term "troche" refers to a small tablet or lozenge (i.e., a medicated candy intended to be dissolved in the mouth), typically in a form of a disk, a ball or rhombic in cross-section, comprising medication and processed into a paste and dried.

The term "therapeutically effective amount" is defined as the amount of a compound or pharmaceutical composition that will elicit the biological or medical response of a tissue, system, animal or human that is being sought by the researcher, medical doctor or other clinician.

The term "pharmaceutically acceptable" when used in the context of a carrier, diluent or excipient, refers to a substance that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

The terms "oral administration" and "orally administering" are broadly defined as a route of administration where a medication is taken through the mouth including "sublingual administration" and "buccal administration" where the medication is placed under the tongue or between the gums and the cheek, respectively, to be absorbed by the body, or to be administered sublingually or buccally as a liquid.

B. Embodiments of the Invention

According to embodiments of the present invention, there are provided pharmaceutical compositions for anesthetic purposes. The compositions comprise, consist of or consist essentially of, a combination of therapeutically effective quantities of at least one pharmaceutically active compound of the first class and at least one pharmaceutically active compound of the second class. In some further embodiments, the compositions optionally comprise, in addition to the above-mentioned pharmaceutically active compounds of the first and second classes, at least pharmaceutically active compound of the third class.

The pharmaceutically active compound of the first class that is used in such composition comprises a benzodiazepine moiety or pharmaceutically acceptable salts, hydrates, solvates or N-oxides thereof. Those having ordinary skill in the art will know that benzodiazepine moiety is a structure where a benzene ring is condensed with diazepine ring, a seven-member heterocycle with two nitrogen atoms which for the purposes of this specification may be in any positions of the ring (e.g., 1,2-diazepine, 1,3-diazepine or 1,4-diazepine). An example of a compound having benzodiazepine moiety with 1,4-diazepine structure is shown below:

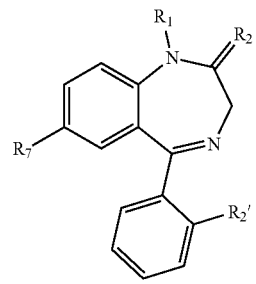

One particular pharmaceutically active compound of the first class comprising a benzodiazepine moiety that can be used in pharmaceutical compositions described and claimed herein is midazolam. Other specific, non-limiting examples of pharmaceutically active compounds of the first class comprising benzodiazepine moiety that can be used include diazepam, lorazepam, flunitrazepam, alprazolam, chlordiazepoxide, clonazepam, clobazam, bromazepam, prazepam, oxazepam and clorazepate. Each of these is also known under one or several trade names as shown in Table 1, which also discloses chemical names of such compounds. Those having ordinary skill in the art can select alternative suitable benzodiazepine-based compound for using in the compositions, if so desired.

TABLE 1

Examples of Benzodiazepine-Based Compounds That Can Be Used in Compositions

| Compound | Chemical Name (IUPAC) | Trade Name(s) |
| --- | --- | --- |
| Midazolam | 8-chloro-6-(2-fluorophenyl)-1-methyl-4H-imidazo[1,5-a][1,4]benzodiazepine | VERSED ®, DORMICUM ®, HYPNOVEL ® |
| Diazepam | 7-chloro-l-methyl-5-phenyl-3H-1,4-benzodiazepin-2-one | VALIUM ®, DIASTAT ® |
| Lorazepam | 7-chloro-5-(2-chlorophenyl)-3-hydroxy-1,3-dihydro-2H-1,4-benzodiazepin-2-one | TEMESTA ®, ATIVAN ®, ORFIDAL ® |
| Flunitrazepam | 5-(2-fluorophenyl)-1-methyl-7-nitro-1H-benzo[e][1,4]diazepin-2(3H)-one | ROHYPNOL ®, NARCOZEP ® and many others |
| Alprazolam | 8-chloro-l-methyl-6-phenyl-4H-[1,2,4]triazolo[4,3-a][1,4]benzodiazepine | XANAX ® |
| Chlordiazepoxide | 7-chloro-2-methylamino-5-phenyl-3H-1,4-benzodiazepine-4-oxide | LIBRIUM ® |
| Clonazepam | 5-(2-chlorophenyl)-7-nitro-2,3-dihydro-1,4-benzodiazepin-2-one | KLONOPIN ®, RIVOTRIL ® and many others |
| Clorazepate | 7-chloro-2,3-dihydro-2-oxo-5-phenyl-1H-1,4-benzodiazepine-3-carboxylic acid | TRANXENE ® |
| Bromazepam | 7-bromo-5-(pyridin-2-yl)-1H-benzo[e][1,4]diazepin-2(3H)-one | LEXOTAN ®, LEXOTANIL ® and many others |
| Oxazepam | 7-chloro-3-hydroxy-5-phenyl-2,3-dihydro-1H-1,4-benzodiazepine-2-one | ALEPAM ®, SERAX ® and many others |
| Clobazam | 7-chloro-l-methyl-5-phenyl-1,5-benzodiazepine-2,4(3H)-dione | URBANOL ®, FRISIUM ®, ONFI ® |
| Prazepam | 7-chloro-1-(cyclopropylmethyl)-5-phenyl-1,3-dihydro-2H-1,4-benzodiazepin-2-one | LYSANXIA ®, CENTRAX ® and many others |

The therapeutically effective quantity of the benzodiazepine-based compound(s) in the entire pharmaceutical composition can be between about 0.2 mass % and about 5.0 mass % of the composition. In some embodiments, the therapeutically effective amount of the benzodiazepine-based compound(s) can be between about 1.0 mass % and about 3.0 mass %, for example, about 2.5 mass % of the composition.

In some applications a patient may be extra sensitive to benzodiazepines (e.g., may become excessively drowsy). For such patients, there are provided additional embodiments of the composition in which benzodiazepine(s)-containing pharmaceutical compositions described above, would additionally include a quantity of a receptor antagonist to benzodiazepines. Such a receptor antagonist would begin counteracting the effect of benzodiazepine after the surgical procedure is complete, in essence providing a slow release feature. A non-limiting example of this antagonist is flumazenil also known under trade names such as ANEXATE®, ROMAZICON® and others. The use of antagonists is also envisioned as a routine practice (i.e., not just for sensitive patients), for example, in situations when a larger than typical or usual dosage of benzodiazepines is medically indicated, or recommended, or necessary. In some further applications, benzodiazepine-based compounds may be used in combination with non-benzodiazepine based sedatives such as eszopiclone, ramelteon, zolpidem, or zaleplon.

The pharmaceutically active compound of the second class that is used in such compositions is an NMDA antagonist, as defined hereinabove, or pharmaceutically acceptable salts, hydrates, solvates or N-oxides thereof. One particular pharmaceutically active compound of the second class that can be used in the pharmaceutical compositions described and claimed herein is ketamine. Other specific, non-limiting examples of NMDA antagonists that can be used include dextrorphan, etomidate, methadone, memantine, amantadine and dextromethorphan. Each of these is also known under one or several trade names as shown in Table 2, which also discloses chemical names of such compounds. Those having ordinary skill in the art can select alternative suitable NMDA antagonists for using in the compositions, if so desired.

embodiments, the combined quantities of both the benzodiazepine-based compound(s) and the NMDA antagonist(s), taken together, in the entire pharmaceutical composition can be between about 1.2 mass % and about 15.0 mass % of the composition, such as between about 3.0 mass % and about 12.0 mass %, for example, about 10.0 mass % of the composition.

As mentioned above, the compositions may further optionally include at least one pharmaceutically active compound of the third class. In such embodiments, the pharmaceutically active compound of the third class is a 0-blocker, as defined hereinabove, or pharmaceutically acceptable salts, hydrates, solvates or N-oxides thereof, or alternatively, and a-2-adrenergic agonist or, as another alternative, a pain reliever. In addition to, or instead of, 13-blockers, the pharmaceutically active compound of the third class may also include an antiemetic medicament, as defined hereinabove, or pharmaceutically acceptable salts, hydrates, solvates or N-oxides thereof In yet another aspect, the pharmaceutically active compound of the third class may include one or several non-steroid anti-inflammatory drug(s) (NSAIDs), as defined hereinabove. NSAID(s) may be so used in addition to, or instead of, 0-blocker(s), and/or antiemetic(s). In a further aspect, the pharmaceutically active compound of the third class may also include an antihistamine medicament, as defined hereinabove. Non-limiting examples of specific antihistamine medicaments that can be so used include, but are not limited to, any of hydroxyzine pamoate, hydroxyzine hydrochloride, diphenhydramine hydrochloride, meclizine, chlorpheniramine, clemastine, promethazine, or prochlorperazine, or any combination thereof. Again, antihistamine medicaments may be used in addition to, or instead of, any of the above-mentioned compounds that may be used as the third pharmaceutically active compound.

The therapeutically effective quantity of the third pharmaceutically active compound(s) in the entire pharmaceutical composition can be between about 0.1 mass % and about 5.0 mass of the composition. In some embodiments, the therapeutic effective amount of the third pharmaceutically active compound(s) can be between about 1.0 mass % and about 4.0 mass %, for example, about 2.5 mass % of the composition.

TABLE 2

Examples of NMDA Antagonists That Can Be Used in Compositions

| Compound | Chemical Name (IUPAC) | Trade Name(s) |
| --- | --- | --- |
| Ketamine | 2-(2-chlorophenyl)-2-(methylamino)cyclohexanone | KETANEST ®, KETASET ®, KETALAR ® (HC1 salt) |
| Dextrorphan | 17-methyl-9a,13a,14a-morphinan-3-ol | None |
| Etomidate | Ethyl-3-[(1R)-1-phenylethyl]imidazole-5-carboxylate | AMIDATE ®, HYPNOMIDATE ® |
| Methadone | 6-(dimethylamino)-4,4-diphenylheptan-3-one | DOLOPHINE ®, AMIDONE ® and others |
| Memantine | 3,5-dimethyladamantan-l-amine | AKATINOL ®, NAMENDA ® and others |
| Amantadine | Adamantan-l-amine | SYMMETREL ® |
| Dextromethorphan | (4bS,8aR,9S)-3-methoxy-11-methyl-6,7,8,8a,9,10-hexahydro-5H-9,4b-(epiminoethano)phenanthrene | ROBITUSSIN ®, DELSYM ® and others |

The therapeutically effective quantity of the NMDA antagonist(s) in the entire pharmaceutical composition can be between about 1.0 mass % and about 10.0 mass % of the composition. In some embodiments, the therapeutically effective amount of the NMDA antagonist(s) can be between about 4.0 mass % and about 6.0 mass %, for example, about 5.0 mass % of the composition. Accordingly, in various One particular f3-blocker that can be used as the pharmaceutically active compound of the third class in pharmaceutical compositions described and claimed herein is metoprolol. Other specific, non-limiting examples of f3-blockers or a-2-adrenergic agonists or pain relievers that can be used include, propranolol, acebutolol, nadolol, atenolol, betaxolol, esmolol, bisoprolol fumarate, carvedilol, nebivolol, penbutolol, timolol, sotalol, dexmedetomidine hydrochloride, and acetaminophen. Each of these is also known under one or several trade names as shown in Table 3, which also discloses chemical names of such compounds. Those having ordinary skill in the art can select alternative suitable f3-blockers for using in the compositions, if so desired.

TABLE 3

Examples of P-Blockers That Can Be Used in Compositions

| Compound | Chemical Name (IUPAC) | Trade Name(s) |
| --- | --- | --- |
| Metoprolol | 1-(isopropylamino)-3-[4-(2-methoxyethyl)phenoxy]propan-2-ol | LOPRESSOR ®, TOPROL ® |
| Propranolol | 1-(1-methylethylamino)-3-(1-naphthyloxy)propan-2-ol | CIPLA ®, INDERAL ® and many others |
| Acebutolol | N-{3-acety1-4-[2-hydroxy-3-(propan-2-ylamino) propoxy]phenyl}butanamide | SECTRAL ®, PRENT ® |
| Nadolol | 5-1[3-(tert-butylamino)-2-hydroxypropyl]oxy}-1,2,3,4-tetrahydronaphthalene-2,3-diol | CORGARD ® |
| Atenolol | 2-{4-[2-hydroxy-3-(propan-2-ylamino)propoxy] phenyl} acetamide | TENORMIN ® |
| Betaxolol | 1-14-[2-(cyclopropylmethoxy)ethy1]-phenoxy}-3-(isopropylamino)propan-2-ol | KERLONE ®, BETOPTIC ® and others |
| Esmolol | 3-{4-[2-hydroxy-3-(propan-2-ylamino)propoxy] phenyl}propanoate | BREVIBLOC ® |
| Bisoprolol fumarate | 1-[4-[[2-(1-methylethoxy)ethoxy]methyl]phenoxy]-3[(1-methylethyl)amino]-2-propano1-2-butenedioate | ZEBETA ® |
| Carvedilol | 3-(9H-carbazol-4-yloxy)-2-hydroxypropy1-2-(2-methoxyphenoxy)ethylamine | COREG ®, CARVIL ® and many other |
| Nebivolol | 2,2'-azanediylbis(1-(6-fluorochroman-2-yl)ethanol) | NEBILET ®, BYSTOLIC ® |
| Penbutolol | 1-(tert-butylamino)-3-(2-cyclopentylphenoxy)propan-2-ol | LEVATOL ®, LEVATOLOL ® and many others |
| Timolol | 1-(tert-butylamino)-3-[(4-morpholin-4-yl-1,2,5-thiadiazol-3-yl)oxy]propan-2-ol | TIMOPTIC ®, BETIMOL ® and many others |
| Sotalol | N-{4-[1-hydroxy-2-(propan-2-ylamino)ethyl]phenyl} methanesulfonamide | BETAPACE ® and others |

One particular antiemetic that can be used as the pharmaceutically active compound of the third class in pharmaceutical compositions described and claimed herein is ondansetron. Other specific, non-limiting examples of antiemetics that can be used include dolasetron, granisetron, palonosetron, promethazine, imenhydrinate, and meclizine. Each of these is also known under one or several trade names as shown in Table 4, which also discloses chemical names of such compounds. Those having ordinary skill in the art can select alternative suitable antiemetics for using in the compositions, if so desired.

TABLE 4

Examples of Antiemetics That Can Be Used in Compositions

| Compound | Chemical Name (IUPAC) | Trade Name(s) |
| --- | --- | --- |
| Ondansetron | (RS)-9-methyl-3-[(2-methyl-1H-imidazol-1-y1)methyl]-2,3-dihydro-1H-carbazol-4(9H)-one | ZOFRAN ®, ONDISOLV ® |
| Dolasetron | (2a,6a,8a,9a(3)-octahydro-3-oxo-2,6-methano-2H-quinolizin-8-y1-1H-indole-3-carboxylate monomethanesulfonate, monohydrate | ANZEMET ® |
| Granisetron | 1-methyl-N-((lR,3r,5S)-9-methy1-9-azabicyclo[3.3.1]nonan-3-y1)-1H-indazole-3-carboxamide | KYTRIL ® |
| Palonosetron | (3aS)-2-[(3S)-1-azabicyclo[2.2.2]oct-3-y1]-2,3,3a,4,5,6-hexahydro-1H-benz[de]isoquinolin-1-one | ALOXI ® |
| Promethazine | (RS)-N,N-dimethyl-1-(1OH-phenothiazin-10-yl)propan-2-amine | PHENERGAN ® |

TABLE 4-continued

Examples of Antiemetics That Can Be Used in Compositions

| Compound | Chemical Name (IUPAC) | Trade Name(s) |
|---|---|---|
| Dimenhydrinate | 2-benzhydryloxy-N,N-dimethylethanamine; 8-chloro-1,3-dimethyl-7H-purine-2,6-dione | DRAMAMINE ®, GRAVOL ®, VOMEX ®, many others |
| Meclizine | (RS)-1-[(4-chlorophenyl)(phenyl)methyl]-4-(3- | BONINE ®, BONAMINE ®, ANTIVERT ®, many others |

Therefore, in various embodiments, the combined quantities of all the pharmaceutically active compounds (i.e., the benzodiazepine-based compound(s), the NMDA antagonist(s), the (3-blocker(s)), and/or the antiemetic(s) taken together, in the entire pharmaceutical composition can be between about 1.3 mass % and about 20.0 mass % of the composition, such as between about 3.0 mass % and about 12.0 mass %, for example, about 10.0 mass % of the composition. Those having ordinary skill in the art will determine the most appropriate quantities of each the pharmaceutically active compound that are within the above-mentioned ranges and that are most suitable for a particular patient. As a non-limiting guideline only, the following mass ratios between the pharmaceutically active compounds may be used (Table 5) for compositions where the benzodiazepine-based compound is midazolam, the NMDA antagonist is ketamine hydrochloride and the f3-blocker is propanolol hydrochloride:

TABLE 5

Exemplary Mass Ratios between Midazolam, Ketamine Hydrochloride and Propanolol Hydrochloride in the Compositions

| Ratios | Midazolam | Ketamine Hydrochloride | Propanolol Hydrochloride |
|---|---|---|---|
| Between about | 1 | 2 | 1 |
| and about | 1 | 10 | 1 |
| Such as between about | 1 | 4 | 1 |
| and about | 1 | 6 | 1 |
| For example | 1 | 5 | 1 |

In one specific embodiment, which is exemplary and non-limiting, for the composition having midozalam as the pharmaceutically active compound of the first class, ketamine as the pharmaceutically active compound of the second class and ondansetron at the third pharmaceutically active compound, the mass midazolam:ketamine:odansetron ratio may be about 3:25:2.

The pharmaceutical compositions described herein may contain not only pharmaceutically active components but also, in some embodiments, may further include one or several inactive, neutral compounds which can be pharmaceutically acceptable excipient(s) or carrier(s), including, but not limited to, binder(s), antioxidant(s), adjuvant(s), synergist(s) and/or preservative(s). The mass concentration of such inactive compounds can be between about 80 mass % and about 99 mass % of the entire pharmaceutical composition, such as between about 85 mass % and about 95 mass %, e.g., about 90 mass %.

Some embodiments of the invention are directed to pharmaceutical formulations that are formulated as solid articles suitable for sublingual or oral administration, such as troches, lozenges, capsules, pills, caps or boluses. These solid compositions typically comprise binder(s) and/or excipient(s). They can be prepared by first mixing the pharmaceutically active compounds described above with suitable binder(s) and/or excipient(s) followed by molding or compressing the blend. Both hard and chewable lozenges and troches are within the scope of the invention.

Typical binder(s) that can be used for fabricating solid articles mentioned above include, without limitation, polyglycols as defined above, such as, e.g., polyethylene glycols (PEGs), polyethylene oxides (POE), methoxypolyethylene glycols, polypropylene glycols, polybutylene glycols or derivatives thereof having a molecular weight that is sufficient to provide the necessary hardness and time for dissolution of the troche; for example, the acceptable molecular weight can be within the range of between about 1,000 Daltons and about 8,000 Daltons. In some embodiments PEG-1450 or PEG-400 can be used. Non-limiting examples of some specific polyglycol derivatives that can be used are:

(a) PEG-laureates and dilaureates (e.g., PEG-10-, PEG-12-, PEG-20-, PEG-32-laurates, PEG-20- and PEG-32-dilaurates, PEG-20-glyceryl-, PEG-30-glyceryl- and PEG-40-glyceryl-laurates, PEG-80-sorbitan laurate);

(b) PEG-oleates, dioleates and trioleates (e.g., PEG-12-, PEG-15-, PEG-20-, PEG-32, PEG-200- and PEG-400-oleates, PEG-20- and PEG-32-dioleates, PEG-20-trioleate, PEG-25-glyceryl trioleate, PEG-20-glyceryl- and PEG-30-glyceryl-oleates, PEG-40-sorbitan oleate);

(c) PEG-stearates and distearates (e.g., PEG-15-, PEG-40-, PEG-100-stearates, PEG-32-distearate and PEG-20-glyceryl stearate);

(d) castor, palm kernel, corn and soya oil derivatives of PEG (e.g., PEG-35-, PEG-40- and PEG-60-castor oils, PEG-40-, PEG-50- and PEG-60-hydrogenated castor oils, PEG-40-palm kernel oil, PEG-60-corn oil, PEG-30-soya sterol);

(e) other PEG derivatives (e.g., PEG-24- and PEG-30-cholesterol, PEG-25-phytosterol, PEG-6- and PEG-8-caprate/caprylate glycerides, tocopheryl PEG-100 succinate, PEG-15-100 octylphenol products and PEG-10-100 nonylphenol products);

(f) other products such as polyglyceryl-10-laurate, POE-9- and POE-23-lauryl ethers, POE-10- and POE-20-oleyl ethers, POE-20-stearyl ether, polysorbates-20 and 80, polyglyceryl-10-oleate, Tween 40, Tween 60, sucrose monostearate, monolaurate and monopalmitate and various products of Poloxamer series.

Typical excipient(s) that can be used for fabricating solid articles mentioned above include, without limitation, gelatin, sodium saccharin, stevioside, peppermint oil, or any natural or artificial fruit, vegetable, flower, beverage or candy flavor.

As stated above, the compositions may optionally further include one or several antioxidant(s). If antioxidant(s) are used, non-limiting examples of those that can be used include a-tocopherol acetate, acetone sodium bisulfite, acetylcysteine, ascorbic acid, ascorbyl palmitate, butylated hydroxyanisole, butylated hydroxytoluene, cysteine, cysteine hydrochloride, tocopherol natural, tocopherol synthetic, dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea and tocopherols.

As stated above, the compositions may optionally further include one or several adjuvant(s) or synergists(s). If adjuvant(s) or synergists(s) are used, non-limiting examples of those that can be used include citric acid, EDTA (ethylenediaminetetraacetate) and salts, hydroxyquinoline sulfate, phosphoric acid and tartaric acid.

As stated above, the compositions may optionally further include one or several preservative(s). If preservative(s) are used, non-limiting examples of those that can be used include benzalkonium chloride, benzethonium chloride, benzoic acid and salts, benzyl alcohol, boric acid and salts, cetylpyridinium chloride, cetyltrimethyl ammonium bromide, chlorobutanol, chlorocresol, chorhexidine gluconate or chlorhexidine acetate, cresol, ethanol, imidazolidinyl urea, metacresol, methylparaben, nitromersol, o-phenyl phenol, parabens, phenol, phenylmercuric acetate/nitrate, propylparaben, sodium benzoate, sorbic acids and salts, f3-phenylethyl alcohol and thimerosal.

According to certain additional embodiments, the pharmaceutical compositions comprise, consist of or consist essentially of, a therapeutically effective quantity of either at least one pharmaceutically active compound of the first class or at least one pharmaceutically active compound of the second class, but not a combination comprising compounds of both the first class and the second class. In such embodiments, the additional presence in the composition of at least one pharmaceutically active compound of the third class is required. Such compositions are defined for the purposes of the present specification as "two-class composition" meaning they only include two particular classes of pharmaceutically active compound and not more.

In other words, according to these additional embodiments the pharmaceutical compositions comprise, consist of or consist essentially of:
 (a) either at least one pharmaceutically active compound of the first class (i.e., one or more of midazolam, diazepam, lorazepam, flunitrazepam, alprazolam, chlordiazepoxide, clonazepam and clorazepate, and pharmaceutically acceptable salts, hydrates, solvates or N-oxides thereof) and at least one pharmaceutically active compound of the third class (i.e., one or more of (3-blockers, antiemetic medicaments, NSAIDs, antihistamines, a-2-adrenergic agonists, pain relievers and combinations thereof, or pharmaceutically acceptable salts, hydrates, solvates or N-oxides thereof); or
 (b) either at least one pharmaceutically active compound of the second class (i.e., one or more of ketamine, dextrorphan, etomidate, methadone, memantine, amantadine, dextromethorphan, and pharmaceutically acceptable salts, hydrates, solvates or N-oxides thereof) and at least one pharmaceutically active compound of the third class.

The vehicle that can be used in such two-class compositions can be the same as described herein for the three-class compositions, and such embodiments do envision the use of in the vehicle such polymers as esters of cellulose (e.g., methyl cellulose or hydroxypropyl methyl cellulose), poly (lactic-co-glycolic acid), polylactic acid, polyglycolide, dextrin, polyacetals, poly(N-(2-hydroxypropyl)methacrylamide), polycaprolactone, and poly-3-hydroxybutyrate. Likewise, the vehicle can contain excipients such as gelatin, sodium saccharin, stevioside, peppermint oil, cherry flavor, lemon oil, raspberry flavor and combinations thereof. The use of extended release capsules ensconcing the pharmaceutical formulation, or matrix polymer structures is also provided for. Any two-class composition can be also formulated as a troche, a lozenge, a capsule, a pill, a cap, and a bolus, as discussed herein.

By using two-class compositions, some unexpected results may be obtained. For example, ondansetron (a compound of the third class) is a medicament having antiemetic properties. Midazolam (a compound of the first class) is not normally considered antiemetic. Yet, surprisingly, a two-class combination of ondansetron and midazolam has antiemetic activity that is markedly better than that of ondansetron alone, which may be indicative of synergy between midazolam and ondansetron.

The pharmaceutical formulations described herein can be administered to a subject in need of conscious sedation, procedural sedation, analgesia and/or pre-sedation, and in general for any kind of non-general anesthesia, by various local administrations. More specifically, the pharmaceutical formulations described herein may be prescribed by ordinarily skilled medical practitioners such as physicians, as the means of conscious sedation or pre-sedation. This is intended to be used for certain patients who experience or expect to experience high anxiety, bouts of panic attacks, disquietude, apprehension, angst or similar feelings of psychological discomfort or distress prior to, or during, medical or surgical procedures as described in more detail below. The patients may be of any age, i.e., including children, adolescents and adults.

For example, the formulation can be used prior to various outpatient surgeries and medical procedures, both invasive and non-invasive, such as an ophthalmic surgery, outpatient medical or surgical procedures, dental procedures, urological procedures, obstetric and gynecological procedures, gastrointestinal procedures, otolaryngological procedures, cosmetic surgery procedures, dermatological procedures, podiatric procedures, orthopedic procedures, emergency medical treatments, psychiatric treatments, and veterinarian procedures.

Specific representative examples of the procedures that are amenable to use of the formulation include, without limitation, cataract surgery, glaucoma surgery, corneal surgery, eyelid surgery, retinal surgery, tooth extraction, oral surgery, root canal surgery, medical imaging procedures (e.g., MRI or CAT scanning, especially for patients suffering from claustrophobia), biopsy, bone marrow harvesting, colonoscopy, endoscopy and laparoscopy.

In one non-limiting embodiment, local administration is by the oral route, such as sublingually or buccally, typically being delivered to the patient in the form of a solid delivery vehicle such as a troche, a lozenge, a capsule, a pill, a cap, and a bolus, as mentioned above. In an additional embodiment, the pharmaceutical composition may be formulated as a liquid item adapted for sublingual or buccal administration (in which case it will include all the pharmaceutically active compounds described above, but no pharmaceutically suitable binder); such liquid formulations may be delivered by any method to be selected by one having ordinary skill in the art of delivery of medications, e.g., via a syringe, dropper or pipette. Such local administration may be used instead of intravenous administration or to complement the latter, as appropriate.

It will be understood by those having ordinary skill in the art that the specific dose level and frequency of dosage for any particular patient may be varied and will depend upon many factors including the activity of the specific compound employed, the metabolic stability and length of action of that compound, the age, body weight, general health, gender, diet and the severity of the particular condition being treated.

In additional embodiments, the pharmaceutical compositions of the present invention may be incorporated into vehicles allowing extended release of the compositions over a period of time. To achieve this effect, the compositions may be combined with polymers forming such vehicles. The product will be extended release capsules ensconcing or enveloping the pharmaceutical formulation, or alternatively, a matrix polymer structure holding the pharmaceutical formulation that is embedded into the matrix.

The vehicle carrying the pharmaceutical formulation may be configured to allow the gradual release of the pharmaceutical formulation over not less than about 12 hours, such as between about 12 hours and about 20 hours, for example, about 16 hours. The rate of release may be uniform throughout the entire period of release; alternatively, those having ordinary skill in the art may formulate the release vehicle in such a way as to allow different rates of release at different times, for example, faster release at the beginning of the process of release and slower at later stages, or vice versa, or in any other way that may be necessary.

The vehicle may be manufactured from any pharmaceutically acceptable polymer that is capable of releasing at least 95 mass % of the pharmaceutical formulation that the vehicle incorporates within the above-mentioned time periods, i.e., within not less than 12 hours, or 1220 hours. In some embodiments, the vehicle may be formulated to ensure the release of at least 97 mass % of the pharmaceutical formulation, for example, at least 99.5 mass %.

Those having ordinary skill in the art will select the most appropriate polymer for making the vehicle. As guidance only, some non-limiting examples of such polymers include, but are not limited to, esters of cellulose, e.g., methyl cellulose and hydroxypropyl methyl cellulose. Other acceptable polymers include, but are not limited to, poly(lactic-co-glycolic acid) (PLGA), polylactic acid, polyglycolide, dextrin, polyacetals, poly(N-(2-hydroxypropyl)methacrylamide), polycaprolactone, and poly-3-hydroxybutyrate.

One particular type of product that can be used in fabricating the vehicle carrying the pharmaceutical formulation may be water-soluble methylcellulose and hydroxypropyl methylcellulose polymers, such as METHOCEL® family of products, for example, a hydroxypropyl methylcellulose product METHOCEL®E4M, 20% METHOCEL®K4M, or 10% METHOCEL®K100 or, alternatively and particularly useful for hot melt extrusion, another hydroxypropyl methylcellulose product AFFINISOL™HPMC (all mentioned hydroxypropyl methylcellulose polymers are available from Dow Chemical Co., Midland, Mich.).

While all the products that include vehicles carrying the pharmaceutical compositions of the present invention are useful for treating all the medical, surgical and other procedures mentioned above, those having ordinary skill in the art may find these systems particularly suitable and advantageous in the treatments of depression (including major depression or treatment-resistant depression), PTSD, alcohol or substance abuse/dependence, suicide prevention, anxiety (including generalized anxiety disorder), personality disorders (inclusive of borderline personality disorder), and related psychiatric and/or psychological disorders, syndromes, symptoms, maladies, and the like.

According to further embodiments, methods for fabricating the above-described pharmaceutical compositions are provided. A one-batch formulation method may be used, where the components of the pharmaceutical formulation can be combined in single container; the components may be added to the container simultaneously or consecutively. Alternatively, a two- or multiple-batch method(s) may be used if desired, where each component of the pharmaceutical formulation can be combined in separate container followed by combining the contents of each container.

In one exemplary, non-limiting procedure, pre-measured quantities of each ingredient in the form of dry powder can be mixed to form a dry blend followed by mixing it with a pre-molten troche base. The composition can then be molded to form a troche.

In additional embodiments, pharmaceutical kits are provided. The kit includes a sealed container approved for the storage of solid pharmaceutical compositions, the container containing one of the above-described pharmaceutical compositions an instruction for the use of the composition and the information about the composition are to be affixed to the container or otherwise enclosed with it.

The following examples are provided to further elucidate the advantages and features of the present invention, but are not intended to limit the scope of the invention. The examples are for the illustrative purposes only. USP pharmaceutical grade products were used in preparing the formulations described below.

Example 1. Preparing a Pharmaceutical Composition in the Form of a Troche

A pharmaceutical composition may be prepared as described below. The following products can be used in the amounts and concentrations specified:
  (a) about 0.2 g of midazolam;
  (b) about 2.0 g of ketamine hydrochloride;
  (c) about 0.2 g of ondansetron hydrochloride;
  (d) about 1 mL of lemon oil flavoring; and
  (e) about 15.5 g of standard troche base (comprising polyglycol 1450, polyglycol 400, gelatin, sodium saccharin and steviaside).

The troche base can be melted at low heat while being stirred; when completely molten, the heat can be turned off with continued stirring. All the dry ingredients, pre-weighed can be added into the molten base followed by adding the flavoring and mixing all components together.

While any shape may be used, a half-moon shaped troche mold can be lightly sprayed with PAM® (or a suitable oil/releasing agent) to cover the entire surface of the mold and the mixture prepared as explained above can then be poured into the mold and allowed to cool and harden at room temperature. A heat gun can then be used to smooth out the surface followed by another round of cooling at room temperature followed by removing the so prepared troche from the mold, placing it into a prescription vial and labeling the vial. The troche is now ready to be administered.

Example 2. Preparing an Extended Release Pharmaceutical Composition

An extended release pharmaceutical composition may be prepared as described below. The following products can be used in the amounts and concentrations specified:

(a) about 3.0 g of midazolam;
(b) about 10.0 g of ketamine hydrochloride;
(c) about 21.0 g of Methocell® 1(100M USP grade powder;
(d) about 100 g of Methocell® E4M premium USP grade powder;
(e) about 15.0 g of microcrystalline cellulose powder; and
(f) 100 clear gelatin capsules size No. 0.

Midazolam and ketamine hydrochloride may be triturated to a fine powdery constituency using standard mortar and pestle. Using the principles of geometric dilution, the rest of ingredients (i.e., the two Methocell® powders and the microcrystalline cellulose powder) may be then mixed in with trituration in the mortar. The use of a V-blender and a powder food coloring may be employed to verify that the mixture is homogenous followed by sieving through an 80 mesh sieve to ensure the evenness or the particle sizes which can then be encapsulated in the clear gelatin capsules (size 0).

Principles of geometric dilution that should be followed, as mentioned above, are well known in the art, but for further guidance may be summarized as follows. A portion of an ingredient of a large quantity (L) is to be mixed into an ingredient of a smaller quantity (S) in small portions. To that end, first a portion of L is to be mixed with a portion of S, the two portions having the same volume as a portion of S thus obtaining a mixture Ml. Then another portion of L is to be mixed with a portion of Ml, the two portions having the same volume. This process is to be continued until the entire quantity of L is used up.

The entire quality of L is not to be added to the entire quantity of S in the expectation that the uniform dispersion can be more expeditiously obtained after brief trituration of the mixture.

Example 3. Preparing a Two-Class Pharmaceutical Composition in the Form of a Troche A two-class pharmaceutical composition may be prepared as described below. The following products can be used in the amounts and concentrations specified:
(a) about 0.3 g of midazolam;
(b) about 0.22 g of ondansetron;
(c) about 0.4 g of *Stevia* powder extract;
(d) about 0.5 mL of artificial flavor marshmallow;
(e) about 0.5 mL of vanilla extract flavor;
(f) about 0.5 g of natural lemon flavor; and
(g) about 13.0 g of troche base.

The troche base can be heated at low heat, and once liquified, the heat can be turned off with continued stirring. All other components provided above can then be carefully added to the melted troche base and mixed together to make a mixture of ingredients.

A troche mold can then be lightly sprayed with PAM oil to cover all the surfaces followed by pouring the mixture into the mold, allowing it to cool, polishing, and cooling it again. It is expected that white opaque troches will be obtained having the smell like vanilla, marshmallow and lemon.

Example 4. Preparing a Two-Class Pharmaceutical Composition in the Form of a Troche A two-class pharmaceutical composition may be prepared as described below. The following products can be used in the amounts and concentrations specified:
(a) about 2.5 g of ketamine;
(b) about 0.22 g of ondansetron;
(c) about 0.4 g of *Stevia* powder extract;
(d) about 0.5 mL of artificial flavor marshmallow;
(e) about 0.5 mL of vanilla extract flavor;
(f) about 0.5 g of natural lemon flavor; and
(g) about 13.0 g of troche base.

The troche base can be fabricated following the procedure described in Example 3.

Although the invention has been described with reference to the above examples, it will be understood that modifications and variations are encompassed within the spirit and scope of the invention. Accordingly, the invention is limited only by the following claims.

What is claimed is:

1. A solid pharmaceutical composition formulated for buccal and/or sublingual administration comprising a therapeutically effective dose of midazolam and a therapeutically effective dose of ketamine.

2. The solid pharmaceutical composition of claim 1, wherein the quantity of the midazolam in the pharmaceutical composition is between about 0.2 mass % and about 5% mass % of the composition.

3. The solid pharmaceutical composition of claim 1, wherein the quantity of the ketamine in the pharmaceutical composition is between about 1.0 mass % and about 10% mass % of the composition.

4. The solid pharmaceutical composition of claim 1, further comprising a third pharmaceutically active compound selected from the group consisting of β-blockers, antiemetic medicaments, NSAIDs, antihistamines, α-2-adrenergic agonists, pain relievers and combinations thereof, or pharmaceutically acceptable salts, hydrates, solvates or N-oxides thereof.

5. The solid pharmaceutical composition of claim 1, wherein the solid dosage form of the composition is selected from the group consisting of a troche, a lozenge, a capsule, a pill, a cap and a bolus.

6. The solid pharmaceutical composition of claim 1, further comprising a binder.

7. The solid pharmaceutical composition of claim 6, wherein the binder is a polyglycol selected from the group consisting of polyethylene glycol, polyethylene oxide, methoxypolyethylene glycol, polypropylene glycol and polybutylene glycol.

8. The solid pharmaceutical composition of claim 6, wherein the binder comprises a product having a molecular weight that is sufficient to provide the necessary hardness and time for dissolution of the solid item, the binder being selected from the group consisting of methoxypolyethylene glycol, polypropylene glycol, polybutylene glycol, PEG-laureates, PEG-dilaureates, PEG-oleates, PEG-dioleates, PEG-trioleates, PEG-stearates, PEG-distearates, castor oil derivatives of PEG, palm kernel oil derivatives of PEG, corn oil derivatives of PEG, soya oil derivatives of PEG, cholesterol derivatives of PEG, phytosterol derivatives of PEG, caprate/caprylate glycerides derivatives of PEG, tocopheryl succinate derivatives of PEG, octylphenol derivatives of PEG, nonylphenol derivatives of PEG, polyglyceryl-10-laurate, polyglyceryl-10-oleate, POE-lauryl ethers, POE-oleyl ethers, POE-stearyl ethers, polysorbates, monostearate, monolaurate and monopalmitate derivatives of sucrose, and products of poly(oxypropylene)-co-poly(propylene oxide) family.

9. The solid pharmaceutical composition of claim 1, further comprising an excipient selected from the group consisting of gelatin, sodium saccharin, stevioside, peppermint oil, cherry flavor, lemon oil, raspberry flavor and combinations thereof.

10. A solid pharmaceutical composition formulated for buccal and/or sublingual administration comprising a therapeutically effective dose of midazolam and a therapeutically effective dose of ketamine, wherein the therapeutically effective dose of midazolam comprises about 3 mg of midazolam and wherein the therapeutically effective dose of ketamine comprises about 50 mg of ketamine.

11. The solid pharmaceutical composition of claim 10, further comprising a third pharmaceutically active compound selected from the group consisting of β-blockers, antiemetic medicaments, NSAIDs, antihistamines, α-2-adrenergic agonists, pain relievers and combinations thereof, or pharmaceutically acceptable salts, hydrates, solvates or N-oxides thereof.

12. The solid pharmaceutical composition of claim 10, wherein the solid dosage form of the composition is selected from the group consisting of a troche, a lozenge, a capsule, a pill, a cap and a bolus.

13. The solid pharmaceutical composition of claim 10, further comprising a binder.

14. The solid pharmaceutical composition of claim 13, wherein the binder is a polyglycol selected from the group consisting of polyethylene glycol, polyethylene oxide, methoxypolyethylene glycol, polypropylene glycol and polybutylene glycol.

15. The solid pharmaceutical composition of claim 13, wherein the binder comprises a product having a molecular weight that is sufficient to provide the necessary hardness and time for dissolution of the solid item, the binder being selected from the group consisting of methoxypolyethylene glycol, polypropylene glycol, polybutylene glycol, PEG-laureates, PEG-dilaureates, PEG-oleates, PEG-dioleates, PEG-trioleates, PEG-stearates, PEG-distearates, castor oil derivatives of PEG, palm kernel oil derivatives of PEG, corn oil derivatives of PEG, soya oil derivatives of PEG, cholesterol derivatives of PEG, phytosterol derivatives of PEG, caprate/caprylate glycerides derivatives of PEG, tocopheryl succinate derivatives of PEG, octylphenol derivatives of PEG, nonylphenol derivatives of PEG, polyglyceryl-10-laurate, polyglyceryl-10-oleate, POE-lauryl ethers, POE-oleyl ethers, POE-stearyl ethers, polysorbates, monostearate, monolaurate and monopalmitate derivatives of sucrose, and products of poly(oxypropylene)-co-poly(propylene oxide) family.

16. The solid pharmaceutical composition of claim 10, further comprising an excipient selected from the group consisting of gelatin, sodium saccharin, stevioside, peppermint oil, cherry flavor, lemon oil, raspberry flavor and combinations thereof.

\* \* \* \* \*